US008634618B2

(12) United States Patent
Zug et al.

(10) Patent No.: US 8,634,618 B2
(45) Date of Patent: Jan. 21, 2014

(54) METHOD AND SYSTEM FOR SURGICAL PLANNING

(75) Inventors: James Andrew Zug, Penryn, CA (US); Micah Aaron Forstein, Topeka, KS (US); Emil Michael Saraga, Jr., Apex, NC (US)

(73) Assignee: FUJIFILM Medical Systems USA, Inc., Stamford, CT (US)

( * ) Notice: Subject to any disclaimer, the term of this patent is extended or adjusted under 35 U.S.C. 154(b) by 139 days.

(21) Appl. No.: 13/422,556

(22) Filed: Mar. 16, 2012

(65) Prior Publication Data

US 2012/0170821 A1 Jul. 5, 2012

Related U.S. Application Data

(63) Continuation of application No. 12/287,311, filed on Oct. 8, 2008, now Pat. No. 8,160,325.

(51) Int. Cl.
*G01K 9/00* (2006.01)

(52) U.S. Cl.
USPC ........... 382/128; 382/130; 382/131; 382/132; 382/154; 600/416

(58) Field of Classification Search
None
See application file for complete search history.

(56) References Cited

U.S. PATENT DOCUMENTS

| 4,436,684 | A | 3/1984 | White |
| 5,682,886 | A | 11/1997 | Delp et al. |
| 5,824,085 | A | 10/1998 | Sahay et al. |
| 6,177,034 | B1 | 1/2001 | Ferrone |
| 7,542,791 | B2 | 6/2009 | Mire et al. |
| 7,855,723 | B2 * | 12/2010 | Preiss et al. ................... 345/419 |
| 2003/0181831 | A1 | 9/2003 | Tanaka et al. |
| 2004/0015070 | A1 | 1/2004 | Liang et al. |
| 2004/0087852 | A1 | 5/2004 | Chen et al. |
| 2004/0102866 | A1 | 5/2004 | Harris et al. |

(Continued)

FOREIGN PATENT DOCUMENTS

| EP | 1 406 203 A2 | 4/2004 |
| JP | 2002-534204 | 10/2002 |

(Continued)

OTHER PUBLICATIONS

Tang, Minh Nhut, "Office Action," for U.S. Appl. No. 12/287,311, filed Oct. 8, 2008, dated Aug. 29, 2011, Alexandria, Virginia.

(Continued)

*Primary Examiner* — Minh N Tang
(74) *Attorney, Agent, or Firm* — Woods Oviatt Gilman LLP

(57) ABSTRACT

A method for surgical planning is disclosed. A set of related two-dimensional (2D) anatomical images or 3D images is displayed. A plurality of anatomical landmarks are identified on the set of anatomical images. A three-dimensional (3D) representation of a parent prosthesis is scaled to match a scale of the 2D anatomical images based at least in part on a relationship between the anatomical landmarks. A 2D representation of the scaled 3D parent prosthesis is displayed on at least one of the 2D anatomical images. A system for surgical planning is also disclosed. The system has a prosthesis knowledge-based information system, a patient anatomical-based information system, a user interface, and a controller. The controller has an anatomical landmark identifier. The controller also has a prosthesis-to-anatomical-feature relator. The controller is configured to display a set of related two-dimensional (2D) anatomical images from the patient anatomical-based information system on the user interface.

21 Claims, 9 Drawing Sheets

(56) References Cited

U.S. PATENT DOCUMENTS

| | | |
|---|---|---|
| 2004/0171924 A1 | 9/2004 | Mire et al. |
| 2005/0038338 A1 | 2/2005 | Bono et al. |
| 2005/0059873 A1 | 3/2005 | Glozman et al. |
| 2005/0069183 A1 | 3/2005 | Ashton |
| 2005/0203384 A1 | 9/2005 | Sati et al. |
| 2005/0216305 A1 | 9/2005 | Funderud |
| 2005/0256389 A1 | 11/2005 | Koga et al. |
| 2005/0259882 A1 | 11/2005 | Dewaele |
| 2006/0098010 A1 | 5/2006 | Dwyer et al. |
| 2007/0032720 A1 | 2/2007 | Koivukangas et al. |
| 2007/0066917 A1 | 3/2007 | Hodorek et al. |
| 2008/0081982 A1 | 4/2008 | Simon et al. |
| 2008/0144773 A1* | 6/2008 | Bar-Zohar et al. ......... 378/98.12 |

FOREIGN PATENT DOCUMENTS

| | | |
|---|---|---|
| JP | 2003144454 | 5/2003 |
| JP | 2006-263241 | 10/2006 |
| JP | 2007-229312 | 9/2007 |
| WO | 00/41626 A1 | 7/2000 |
| WO | 2004/001569 A2 | 12/2003 |
| WO | 2004001569 | 12/2003 |
| WO | WO2006/092600 A1 | 9/2006 |

OTHER PUBLICATIONS

Paquit, Vincent, et al, "Near-infrared imaging and structured light ranging for automatic catheter insertion." Medical Imaging 2006: Visualization . . . , Proc.ofSPIEv.6141 61411T.

Biocomputing Competence Centre, "Hip-Op PreOperative Planning. Hip-OpRX." www.hipop.it/hipoprx.html. 2007. pp. 1-2. Casalecchio di Reno (Bo), Italia.

Biocomputing Competence Centre, "Hip-Op PreOperative Planning. HipOpCT: CT Scan Protocol." www.hipop.it/CT_protocol.html. 2007. pp. 1-2. Casalecchio di Reno (Bo), Italia.

Shaw, Grant, "Digital Templating." www.orthoview.com/. 2005. pp. 1-4. Meridian Technique Ltd., Southampton Hampshire, UK.

Artikis, T., "Extended European Search Report," for application No. EP 090 01 2767, filed Oct. 8, 2009, dated Apr. 20, 2011, Munich, Germany.

Gokan, Toichiro, "Notification of Reasons for Rejection," for Japanese Patent Application No. 2009-234540, filed Oct. 8, 2009, mailed Jul. 30, 2013, Kasumigaseki, Chiyoda, Tokyo (including Partial Translation).

* cited by examiner

METHOD AND SYSTEM FOR SURGICAL PLANNING

CROSS-REFERENCE TO RELATED APPLICATIONS

This application is a continuation of U.S. patent application Ser. No. 12/287,311, filed Oct. 8, 2008, now U.S. Pat. No. 8,160,325, which is hereby incorporated by reference in its entirety.

TECHNICAL FIELD

The claimed invention relates to methods for surgical planning, and more particularly to a method and system for surgical planning using a two-dimensional interface based on three-dimensional models and information.

BACKGROUND OF THE INVENTION

As the baby boomer generation ages, the number of hip replacement surgeries is expected to increase. In 2001, about 165,000 hip joints were replaced in U.S. hospitals according to the National Center for Health Statistics, and 326,000 knees were replaced. While the majority of joint replacement patients remain in the 60-plus year category, more people are deciding to have surgery one or two decades earlier.

About 70 percent of people seeking hip replacement surgery have severe osteoarthritis, a common chronic disease that damages cartilage, a type of tissue that acts as a protective cushion allowing for the smooth, low-friction movement of the joint. Osteoarthritis is the leading cause of long-term knee damage and the most common reason for knee replacement. By age 65, women are five times more likely than men to have this disease.

A common goal for physicians when replacing joints is to minimize the discomfort and the recovery time, and reduce the time it takes to successfully install the joint implant while properly installing the new joint to provide the best possible range of motion for the patient using materials and techniques which will maximize the lifetime of the replacement joint. To this end, pre-surgery planning is an important step in the joint replacement process so that the surgeon is able to properly select the best joint replacement option and estimate how it will fit prior to the actual surgery.

Unfortunately, many current planning techniques rely on two-dimensional acetate portrayals of a prosthetic devise implanted which is then overlaid on the patient's two-dimensional x-ray. For example, for hip replacements, commonly used current planning methods for acetabular implant placement and size selection is performed using acetate templates and a single anterior-posterior x-ray of the pelvis. Acetabular templating is mostly performed to determine the approximate size of the acetabular component, but there is little effort to accurately determine the ideal position of the implant prior to surgery. Even implant selection for fit and fill with acetates can be problematic since the subject's x-ray may be rotated compared to the ideal view plane assumed when the acetate was created.

Discrepancies in implant size and placement which remain undetected during planning can lead to longer and more traumatic surgeries as originally intended prosthesis are removed and alternative prosthesis are used to correct misalignments which only become apparent after the operation has begun. Many discrepancies between the desired and actual implant placement can go unnoticed, possibly resulting in reduced range of motion, impingement and subsequent dislocation, or premature joint wear. For example, the incidence of dislocation following primary total hip replacement (THR) surgery is between 2-6% and even higher following revisions. It is, therefore, one of the most commonly occurring complications following hip replacement surgery. Dislocation of a total hip replacement causes significant distress to the patient and physician and is associated with significant additional costs in order to relocate the hip. Another complication of THR surgery is impingement between the neck of the femoral implant and the rim of the acetabular component. Impingement can lead to advanced wear of the acetabular rim resulting in polyethylene wear debris shown to accelerate loosening of implant bone interfaces. The position at which impingement occurs is determined by the design and geometry of the implants (such as the size of the femoral head, the width of the neck, and the design of the acetabular liner), and more importantly by the relative position of the femoral and acetabular implants. In certain cases, impingement may result in dislocation. Therefore, it is highly desirable to have a method and a system which more accurately enables physicians to plan for surgical joint replacement.

With the increasing use of computers in society, surgical planning solutions for joint replacement have been developed which will display a two-dimensional (2D) slice of a three-dimensional (3D) prosthetic on a 2D image. While this 2D slice can be scaled and rotated electronically, the physician is not assured of choosing the correct rotation or orientation.

Therefore, despite advances in computer planning software, there is still a need for methods and systems that more accurately enable physicians to plan.

SUMMARY OF THE INVENTION

A method for surgical planning is disclosed. A set of related two-dimensional (2D) anatomical images is displayed. A plurality of anatomical landmarks are identified on the set of 2D anatomical images. A three-dimensional (3D) representation of a prosthesis is scaled to match a scale of the 2D anatomical images based at least in part on a relationship between the anatomical landmarks. A 2D representation of the scaled 3D prosthesis is displayed on at least one of the 2D anatomical images.

A system for surgical planning is also disclosed. The system has a prosthesis knowledge-based information system, a patient anatomical-based information system, a user interface, and a controller. The controller has an anatomical landmark identifier. The controller also has a prosthesis-to-anatomical-feature relator. The controller is configured to display a set of related two-dimensional (2D) anatomical images from the patient anatomical-based information system on the user interface. This knowledge-based information system guides the selection and placement of implants and excludes implant lines contra-indicated. In addition, the knowledge based information system is updated by the clinical cases planned.

A set of machine executable instructions embodied on a machine readable medium for surgical planning are further disclosed. The set of machine executable instructions include instructions displaying a set of related two-dimensional (2D) anatomical images. The set of machine executable instructions also include instructions identifying a plurality of anatomical landmarks on the set of 2D anatomical images. The set of machine executable instructions further include instructions scaling a three-dimensional (3D) representation of a prosthesis to match a scale of the 2D anatomical images based at least in part on a relationship between the anatomical landmarks. The set of machine executable instructions also include instructions displaying a 2D representation of the scaled 3D prosthesis on at least one of the 2D anatomical images.

Figure 1:
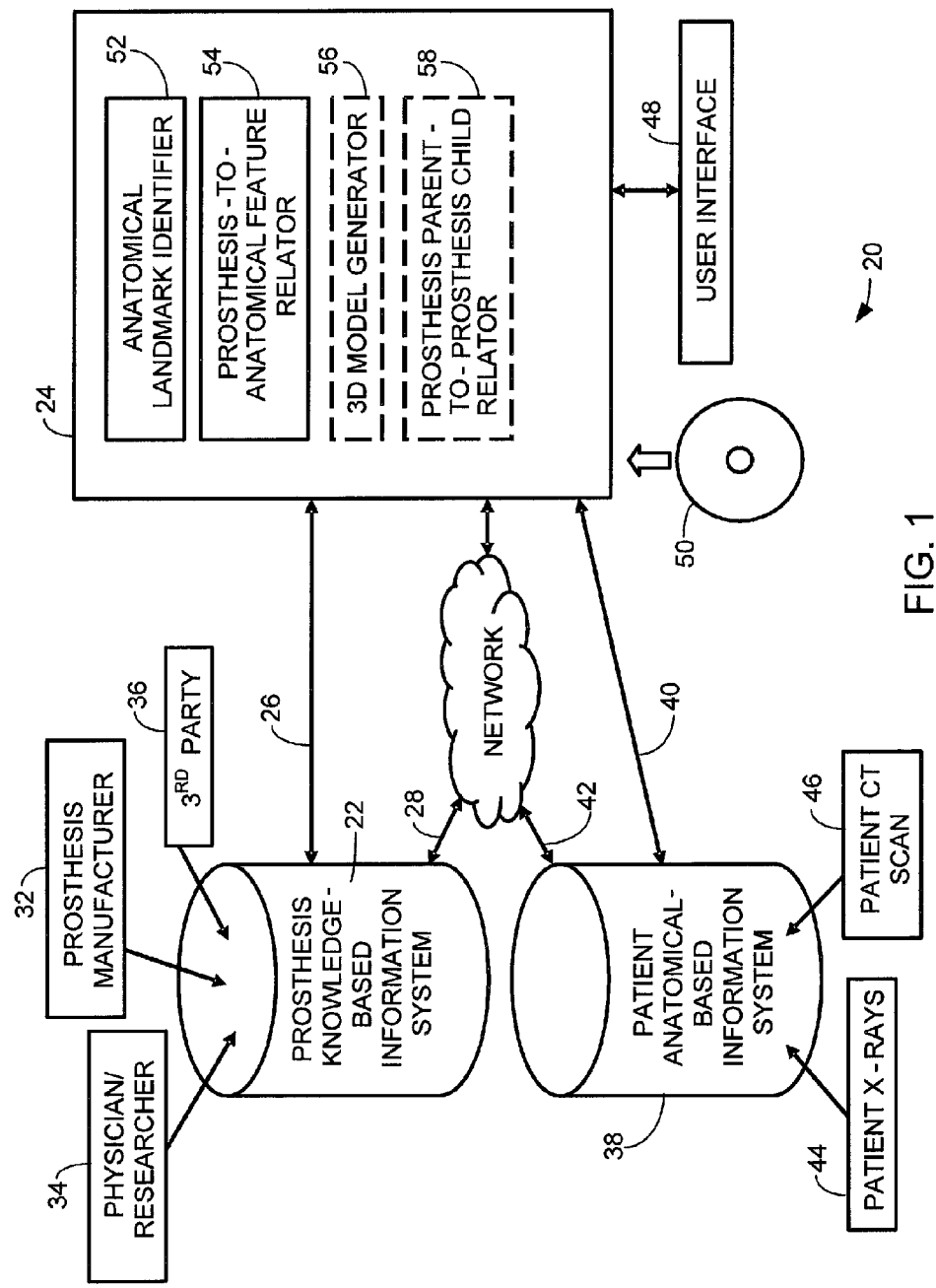
FIG. 1 schematically illustrates one embodiment of a system for surgical planning.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION OF THE INVENTION

FIG. 1 schematically illustrates one embodiment of a system 20 for surgical planning. The system 20 has a prosthesis knowledge-based information system 22. In some embodiments, the prosthesis knowledge-based information system 22 may be a stand-alone database or set of machine-readable files which are directly accessible 26 or remotely accessible 28, for example via a network 30, by the system's controller 24. In other embodiments, the prosthesis knowledge-based information system 22 may be a locally or internally available database or set of machine readable files. The prosthesis knowledge-based information system 22 may exist on a variety of computer readable media, including, but not limited to, randomly accessible memory (RAM), read-only memory (ROM), re-writeable flash memory, magnetic media, and optically readable/writeable media such as CD's and DVD's, or any combination thereof. The one or more computer readable media for the prosthesis knowledge-based information system 22 may be permanently installed in the system 20 or removeably installed.

The prosthesis knowledge-based information system 22 stores three-dimensional (3D) information associated with one or more prostheses. For example, the prosthesis knowledge-based information system 22 may store information defining the volume, surface area, and shape of a prosthesis. Related anatomical information for the prosthesis may also be stored, such as definitions of rotation points for the prosthesis or one or more mechanical axes for the prosthesis. The prosthesis knowledge-based information system 22 may store display information for the prosthesis, such as notes on the usage and features of the prosthesis and measurements of the prosthesis. The prosthesis knowledge-based information system 22 may also store specific locations related to the prosthesis model which can be displayed on the model. The prosthesis knowledge-based information system 22 may further store prosthesis material information. In other embodiments, the prosthesis knowledge-based information system 22 may store information which defines how one prosthesis (parent prosthesis) relates to another prosthesis (child prosthesis). Positional information for two or more related prostheses may be defined, prescribing their necessary locations relative to each other when used together and any possible degrees of freedom when moveable relative to one another. In other embodiments, the prosthesis knowledge-based information system 22 may store information that defines the contra-indications for use of the prosthesis and relates this information to the anatomic landmarks defined. In other embodiments, the prosthesis knowledge-based information system 22 will be updated using statistical relationships formed by the planning process, for different patient plans and by the clinician using the system.

Figure 2:
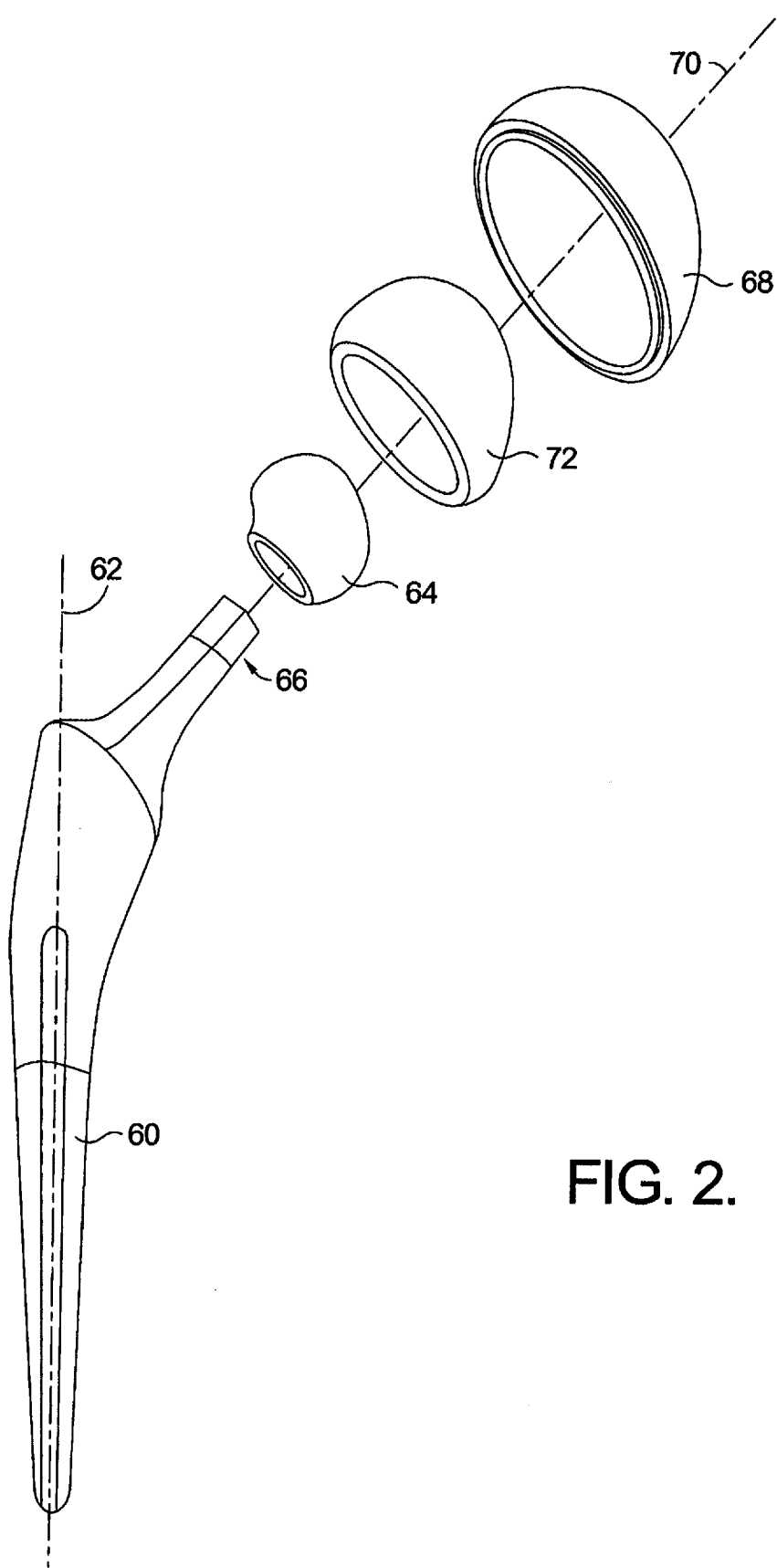
FIG. 2 schematically illustrates an embodiment of a prosthesis.

For example, FIG. 2 illustrates one embodiment of several prosthesis elements which may be used in a hip replacement. A prosthesis stem 60 may be defined as a parent prosthesis, and its surface area, volume, and shape stored in the prosthesis knowledge-based information system 22. The prosthesis stem may have a mechanical axis 62 which is definable and displayable within the system 20. In this embodiment, one of the other prosthesis elements is a prosthesis ball 64 which attaches to the neck 66 of the prosthesis stem. In this case, the ball 66 may be defined as a child prosthesis of the parent stem prosthesis 60, since the position of the ball 66 will be constrained by the position of the stem 60. A further prosthesis element in this embodiment is an acetabular cup 68 which can be installed in a pelvis socket. The acetabular cup 68 may have an associated center of rotation 70. Another prosthesis element in this embodiment is a bearing liner 72 which fits within the acetabular cup 68 to provide a bearing surface for the ball 64. The bearing liner 72 may be defined as a child prosthesis of the acetabular cup 70 or as a child of the stem 60 via the ball 64. Similarly, the acetabular cup 70 may be defined as a child of the stem 60 via the ball 64 and the bearing liner 72 or as its own parent prosthesis having a defined relationship to the stem parent prosthesis. The relationship specified in the prosthesis knowledge-based information system 22 regarding the various parent and child prostheses defines how they interrelate to each other and how they are fixed or may move relative to each other.

Returning to FIG. 1, the information stored in the prosthesis knowledge-based information system 22 may be updated or provided by a prosthesis manufacturer 32 or by a physician, clinician, or researcher 34. In other embodiments, the information stored in the prosthesis knowledge-based information system 22 may be provided by a third party 36, such as a service provider which is able to model existing prostheses for manufacturers or physicians who do not have that capability.

The system 20 for surgical planning also has a patient anatomical-based information system 38. In some embodiments, the patient anatomical-based information system 38 may be a stand-alone database or set of machine-readable files which are directly accessible 40 or remotely accessible 42, for example via a network 30, by the system's controller 24. In other embodiments, the patient anatomical-based information system 38 may be a locally or internally available database or set of machine-readable files. The patient anatomical-based information system 38 may exist on a variety of computer readable media, including, but not limited to, randomly accessible memory (RAM), read-only memory (ROM), re-writeable flash memory, magnetic media, and optically readable/writeable media such as CD's and DVD's, or any combination thereof. The one or more computer readable media for the patient anatomical-based information system 38 may be permanently installed in the system 20 or removeably installed.

The patient anatomical-based information system 38 stores information associated with the anatomy of one or more patients. This may include patient images such as x-rays 44 or a CT scan 46. The anatomical information stored in the patient anatomical-based information system 38 may also include anatomical landmarks and/or anatomical mechanical axes associated with one or more of the patient images. The patient anatomical-based information system 38 may also store notes on the patient as provided by a physician or other medical practitioner for example via a user interface 48 and/or the controller 24. The patient anatomical-based information system 38 may further store a link for each patient to one or more prostheses which have been selected for possible implantation in the patient from the prosthesis knowledge-based information system 22. Furthermore, the patient anatomical-based information system 38 may store information based on the patient's images 44, 46 and the associated one or more prostheses which is generated by the controller 24 during operation of the system 20. The specific types of information related to surgical planning which the system 20 may develop will be discussed in more detail below as such functionality is discussed.

The system also has a processor 24 which is capable of executing machine readable instructions, for example from a machine readable medium 50. Non-limiting examples of a machine readable medium 50 include a diskette, a hard drive, an optical drive, a magnetic drive, a CD, a DVD, a flash memory, a RAM, a ROM, or any combination thereof. The machine readable medium 50 may be removable from the controller, remotely available to the controller 24, permanently installed in the controller 24, or integrated with the controller 24. The controller 24 may be a microprocessor, computer, application specific integrated circuit (ASIC), analog circuitry, digital circuitry, or any combination or plurality thereof. The controller 24 may be a single unit or may be a distributed device.

Figure 3:
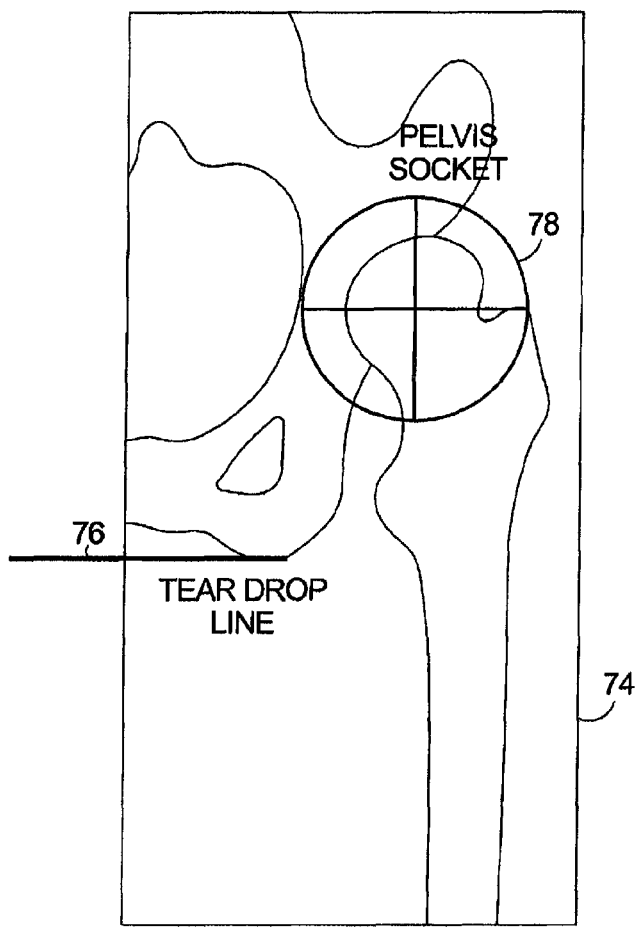
FIG. 3 schematically illustrates an embodiment of anatomical landmarks identified on a two-dimensional image.

The system 20 displays a set of related two-dimensional (2D) anatomical images on the user interface 48. The set of related 2D images may, for example, be patient x-rays or images from a patient CT scan. Multiple images from the set of related 2D anatomical images may be displayed on the user interface at a time, or a single image may be displayed at a time. The controller 24 has an anatomical landmark identifier 52. The actual anatomical landmarks which may be of interest can vary depending on the particular prosthesis being considered and the associated anatomy that the prosthesis would be replacing. In the case of a hip replacement, for example, the anatomical landmarks of interest may include a pelvis socket, a tear drop line, a greater troph cantor, a lesser troph cantor, a femoral head, and an anatomical mechanical axis. In some embodiments, the anatomical landmark identifier 52 is configured to enable a user to identify one or more anatomical landmarks manually by indicating the position of the landmark in one or more images presented on the screen. In other embodiments, the anatomical landmark identifier 52 may be configured to automatically identify some anatomical landmarks. Various automatic landmark identification methods are known to those skilled in the art. In further embodiments, the anatomical landmark identifier 52 may be configured to identify anatomical landmarks using a combination of manual and automatic methods. The anatomical landmark identifier 52 may also be configured to enable the entry of measurements on the patient images for a representation of scale. FIG. 3 illustrates an example of two anatomical landmarks that have been identified on a two-dimensional anatomic image 74. The tear drop line 76 represents the true tilt/rotation of the pelvis within the anterior/posterior image. The pelvis socket marker 78 is the center of rotation of the femur within the pelvis. The one or more 2D images 74 which are displayed to a user of the system may be original 2D images, such as x-rays or a 2D image slice from a 3D CT image set.

Figure 4:
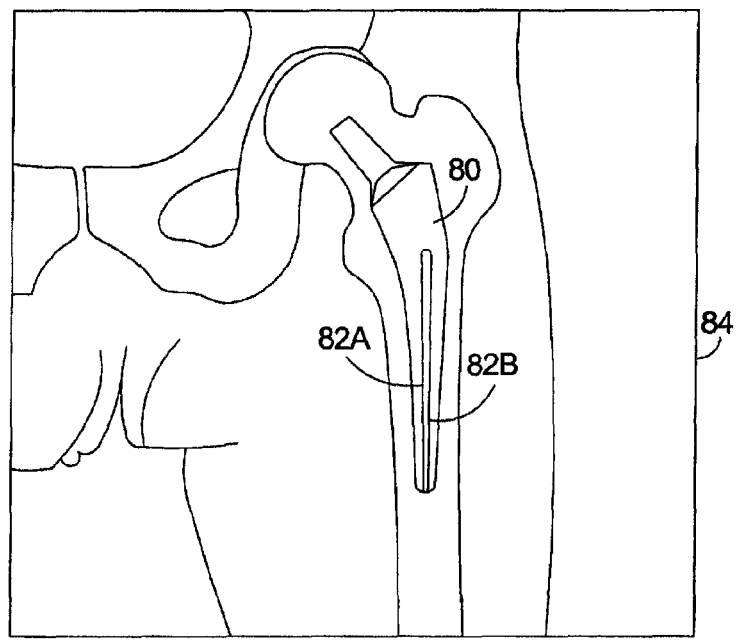
FIG. 4 illustrates an embodiment of a user interface displaying a two-dimensional representation of a three-dimensionally scaled prosthesis.

Returning to FIG. 1, the controller 24 is configured to allow a user to select one or more desired prostheses from the prosthesis knowledge-based information system 22. A 2D or 3D representation of the 3D prosthesis is displayed on the one or more patient images in the user interface 48. The controller 24 also has a prosthesis-to-anatomical-feature relator 54. The prosthesis-to-anatomical-feature relator 54 may be configured to scale the 3D prosthesis to match the scale of the anatomic image prior to creating the 2D or 3D representation. The prosthesis-to-anatomical-feature relator 54 may determine the scale of the image based on measurements from the anatomical landmark identifier 52. As an example, FIG. 4 illustrates an embodiment of a user interface displaying a two-dimensional representation of a three-dimensionally scaled prosthesis 80. The scaled prosthesis 80 may also include feature elements 82A, 82B which may schematically indicate one or more axes of rotation for the prosthesis 80. The user interface 48 may be configured to allow the scaled prosthesis 80 to be moved around within the image 84.

Figure 5:
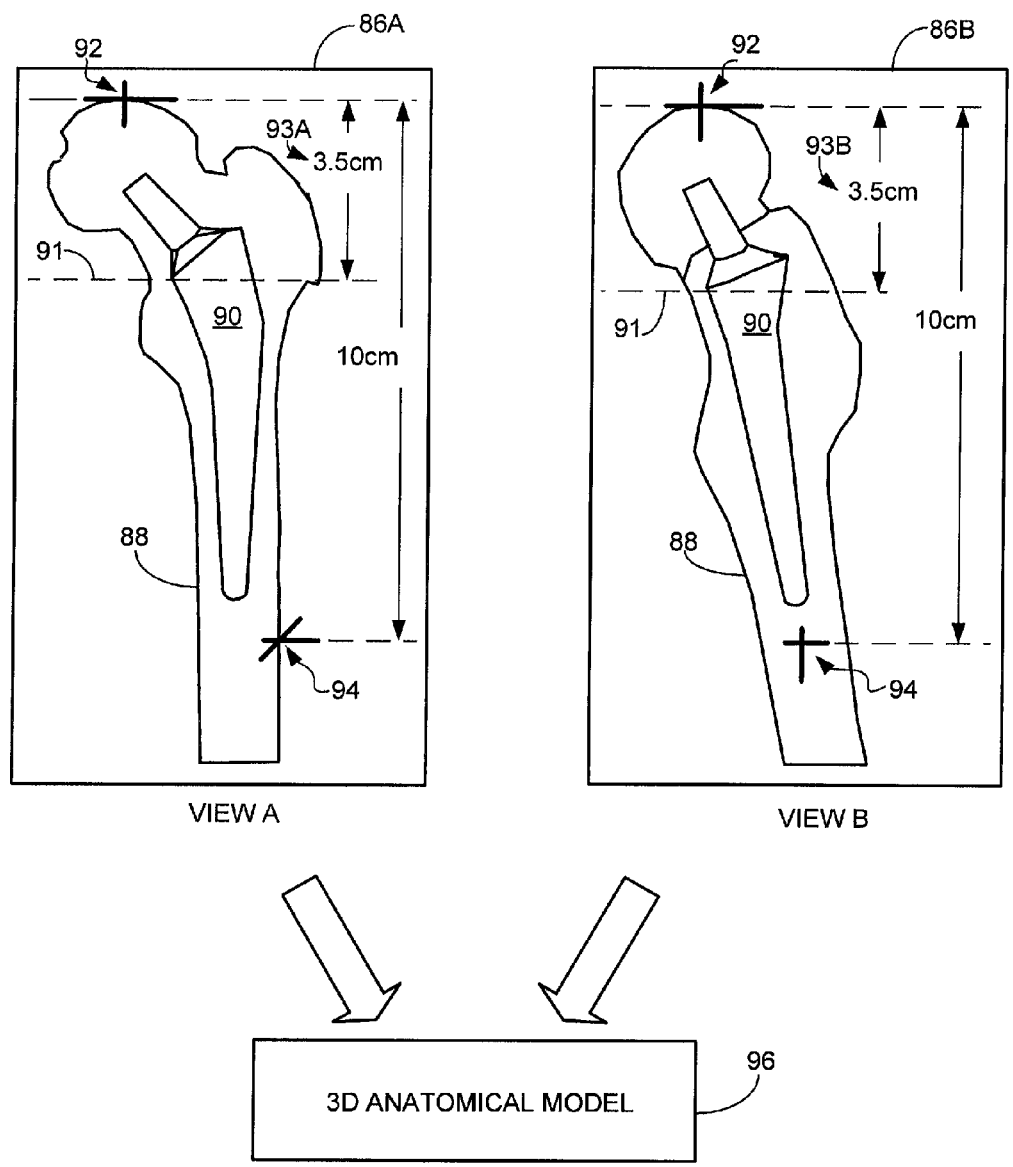
FIG. 5 schematically illustrates embodiments of two-dimensional anatomical images from different perspectives.

Returning to FIG. 1, the system may optionally have a 3D model generator 56. The 3D model generator 56 may be configured to utilize at least two images from the set of related 2D anatomical images to create a 3D anatomical model. FIG. 5 schematically illustrates two 2D anatomical images of a femur 88 having a 2D representation of a 3D prosthesis 90 overlaid on each of the views 86A, 86B. For ease of explanation, two anatomical landmarks 92, 94 have been identified on the views, and a scale between the anatomical landmarks 92, 94 determined. Based on a determination of the angular differences between the views 92, 94, a knowledge of the scale, and a knowledge of the location of one or more anatomical landmarks, the 3D model generator can develop a fit of the known points to a variety of known 3D anatomical models or modify a closest-fit 3D model so that it complies with the known constraints from the 2D images. The result is a 3D anatomical model 96 which can be used for more accurate surgical planning. Various techniques are known to those skilled in the art to produce a three-dimensional model from a set of two-dimensional images. The 3D anatomical model 96 may include the anatomical landmarks 92, 94 located in 3D. Furthermore, the prosthesis-to-anatomical-feature relator 54 may display the relationship between the anatomical landmarks located in 3D to the 3D parent prosthesis. For example, a hypothetical reference line on the prosthesis 90, such as a cut-line 91 may be automatically referenced relative to an anatomical landmark such as femur head 92. The distances relative to the cut line may be displayed, for example as in 93A, 93B, and 93C.

Figure 6:
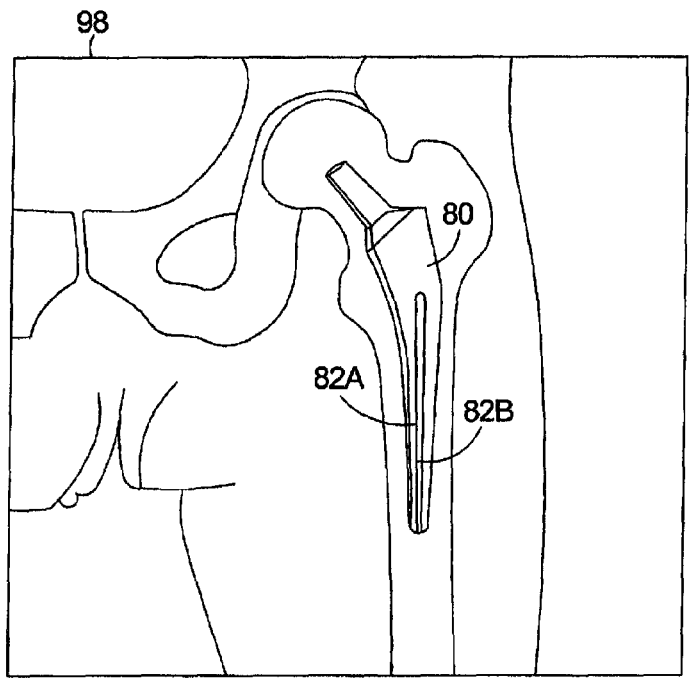
FIG. 6 illustrates an embodiment of a user interface displaying a two-dimensional representation of a rotated version of the three-dimensionally scaled prosthesis of FIG. 4.

Embodiments which develop a 3D anatomical model 96 may also be configured to enable the prosthesis-to-anatomical-feature relator 54 to determine a 3D relationship between the 3D anatomical model 96 and a 3D prosthesis model from the prosthesis knowledge-based information system 22. By determining the relationships in three-dimensions the prosthesis-to-anatomical-feature relator 54 may then develop highly accurate 2D representations of the 3D relationship which do not suffer from the limitations of the prior art which have been discussed above. Utilizing the accurate 3D relationships between the anatomical model 96 and the prosthesis, the system may be configured not only to move the prosthesis within the different images, but to rotate the prosthesis, for example, with six degrees of freedom. The rotation may also optionally be constrained to a desired axis, for example a mechanical axis of the prosthesis. FIG. 6 illustrates an embodiment of a user interface displaying a two-dimensional representation of a rotated version of the three-dimensionally scaled prosthesis of FIG. 4. The axis lines 82A, 82B from FIG. 4 have been aligned in the view of FIG. 6, while the prosthesis 80 in the 2D view 98 has been accurately adjusted based on the 3D calculations based on the relationship between the 3D anatomical model 96 and the 3D prosthesis model.

Figure 7:
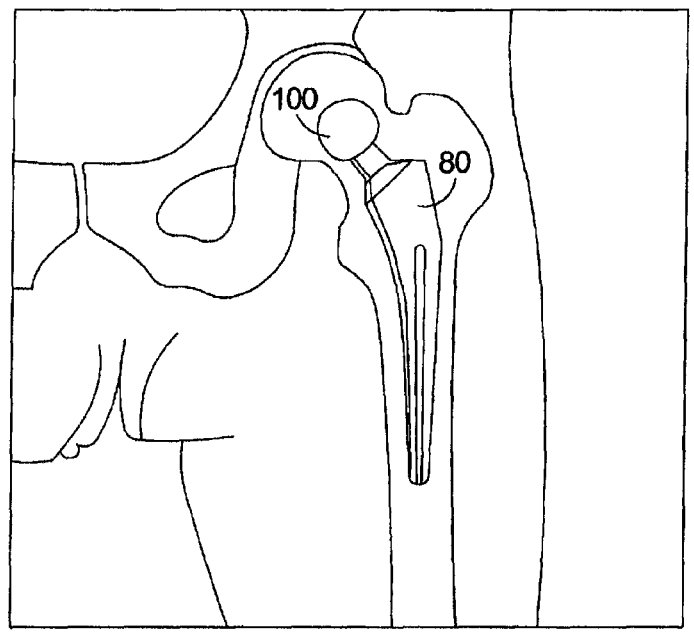
FIG. 7 illustrates an embodiment of a user interface displaying a two-dimensional representation of a three-dimensionally scaled child prosthesis in relation to the prosthesis of FIG. 5.
Figure 8:
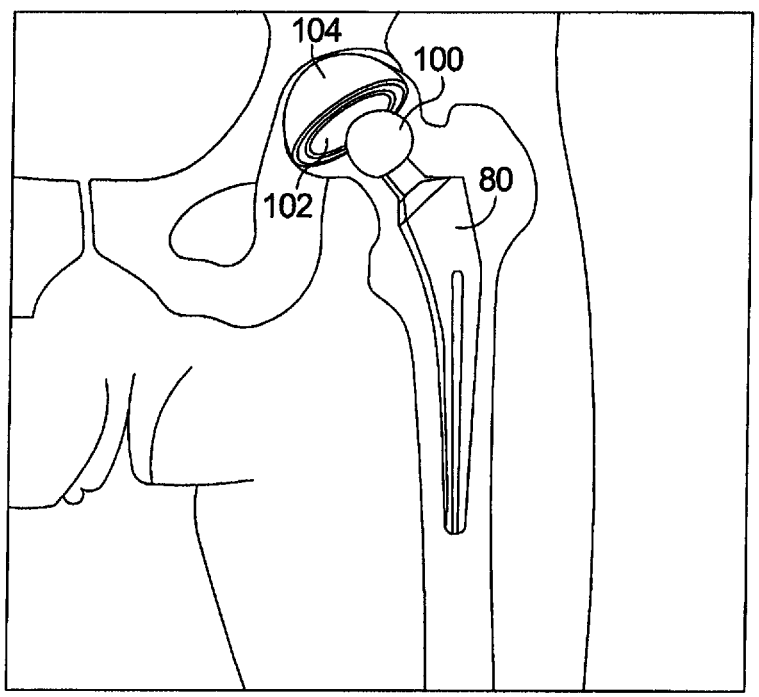
FIG. 8 illustrates an embodiment of a user interface displaying two-dimensional representations of multiple three-dimensionally scaled prostheses.

Returning to FIG. 1, the processor 24 may optionally have a prosthesis-parent-to-prosthesis-child relator 58. The prosthesis-parent-to-prosthesis-child relator 58 may be configured to determine a 3D relationship between a parent prosthesis model and a child prosthesis model from the prosthesis knowledge-based information system 22 as well as from the 3D anatomical model. As FIG. 7 illustrates, once the parent prosthesis 80 has been placed and its position is known in 3D, a child prosthesis 100 may be included in the 3D model according to its constraints. In the case of child prosthesis 100 (a ball), the child prosthesis is fixed relative to the parent prosthesis 80 (a stem). The system 20 is able to display an accurate 2D representation of this 3D relationship, and the surgical planner operating the system 20 only has to move the parent to create a corresponding move in the child. FIG. 8 illustrates the idea that there may be multiple children prostheses 100, 102, 104 which may be associated to a parent prosthesis 80. The prosthesis knowledge-based information system 22 may define the range of motion between various prosthesis, so that, in this example the bearing liner 102 and acetabular cup 104 could be manipulated within the image only to locations compatible with the ball 100 and stem 80 location. In other embodiments, certain prostheses may be defined in the prosthesis knowledge-based information system 22 as both a parent and as a child prosthesis. For example, the acetabular cup 104 of FIG. 8 could be configured as a parent prosthesis which is moved into position relative to the 3D anatomical model independently of other prostheses. The bearing liner 102 could be a child prosthesis of the acetabular cup 104. Independent from that, the stem 80 could be a separate parent prosthesis which defines where ball 100 will end up. At some point, however, it may be useful to understand the relationship between the ball/stem combination 80,100 and the cup/liner combination 102,104. In this case, the cup 104 and liner 102 may be made child prostheses of the stem prosthesis for the purpose of determining whether the chosen placement is within a desired specification. If the placement of the prosthesis does not fall within the allowed relationship specified by the prosthesis knowledge-based information system 22, then a warning could be displayed to the user or a corrective shift could be forced on the prosthesis. If the chosen implant is contra-indicated based upon the prosthesis knowledge-base information system 22, and the anatomic landmarks defined then a warning could be displayed to the user and an alternative could be suggested.

The system 20 and its equivalents provide a medical practitioner with the ability to effectively plan a surgical procedure by allowing them to test-fit various prostheses from the prosthesis knowledge-based information system 22 on a 2D or a 3D anatomical model of a subject patient. Performing the relational calculations in three-dimensions before creating the two-dimensional representations for view by the user ensure that differences in rotation, scaling, and perspective are taken into account.

Figure 9:
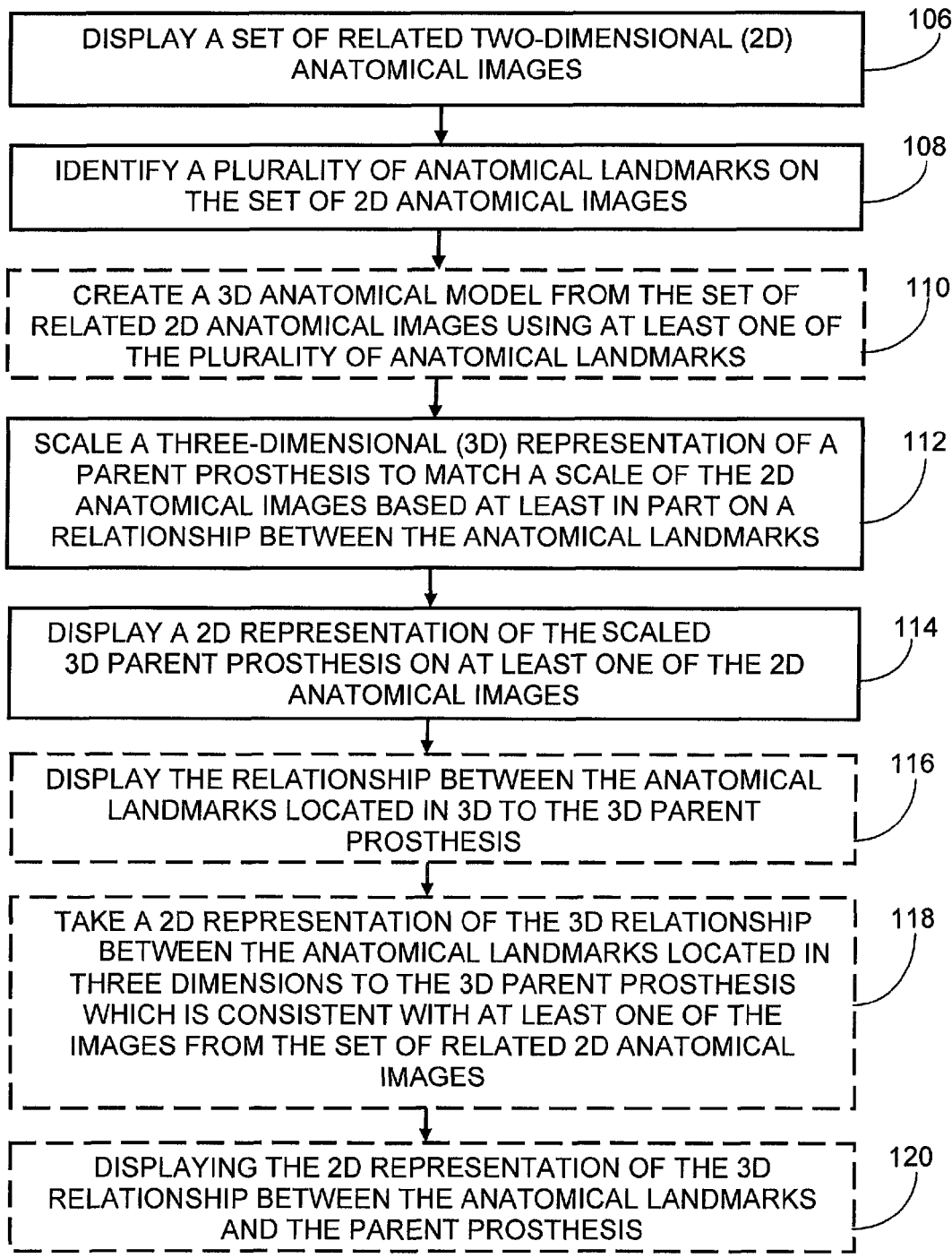
FIG. 9 illustrates one embodiment of a method for surgical planning.

FIG. 9 illustrates one embodiment of a method for surgical planning. A set of related two-dimensional (2D) anatomical images are displayed 106. The set of images may be displayed all at the same time, one at a time, or more than one at a time via a user interface. The 2D images may come from a variety of 2D or 3D sources, such as x-rays or a CT Scan. A plurality of anatomical landmarks are identified 108 on the set of 2D anatomical images. If the 2D anatomical images came from a 3D image set, then a 3D anatomical model may already be available. Optionally, however, a 3D anatomical model may be created 110 from the set of related 2D anatomical images using at least the plurality of anatomical landmarks. The anatomical landmarks can be used to provide scaling information as well as to provide known points that can be fit into the 3D anatomical model.

A three dimensional (3D) representation of a parent prosthesis is scaled 112 to match a scale of the 2D anatomical images based at least in part on a relationship between the anatomical landmarks. A 2D representation of the scaled 3D parent prosthesis is displayed 114 on at least one of the 2D anatomical images. The prosthesis may be rotated or moved based on calculations done in three dimensions, and the correspondingly-adjusted 2D representation of this new position will be displayed.

Optionally, the relationship between the anatomical landmarks located in 3D to the 3D parent prosthesis may be displayed 116. Such relationships may provide measurements and reference points for the surgical plan.

Optionally, an alternate 2D representation of the 3D relationship between the anatomical landmarks located in three dimensions to the 3D parent prosthesis may be taken 118 which is different from the views present in the displayed set of anatomical images. This step is effectively creating a 2D slice of the 3D anatomical model and the related and scaled 3D prosthesis model from a different perspective than was originally available. The alternate 2D representation may optionally be displayed 120.

Figure 10:
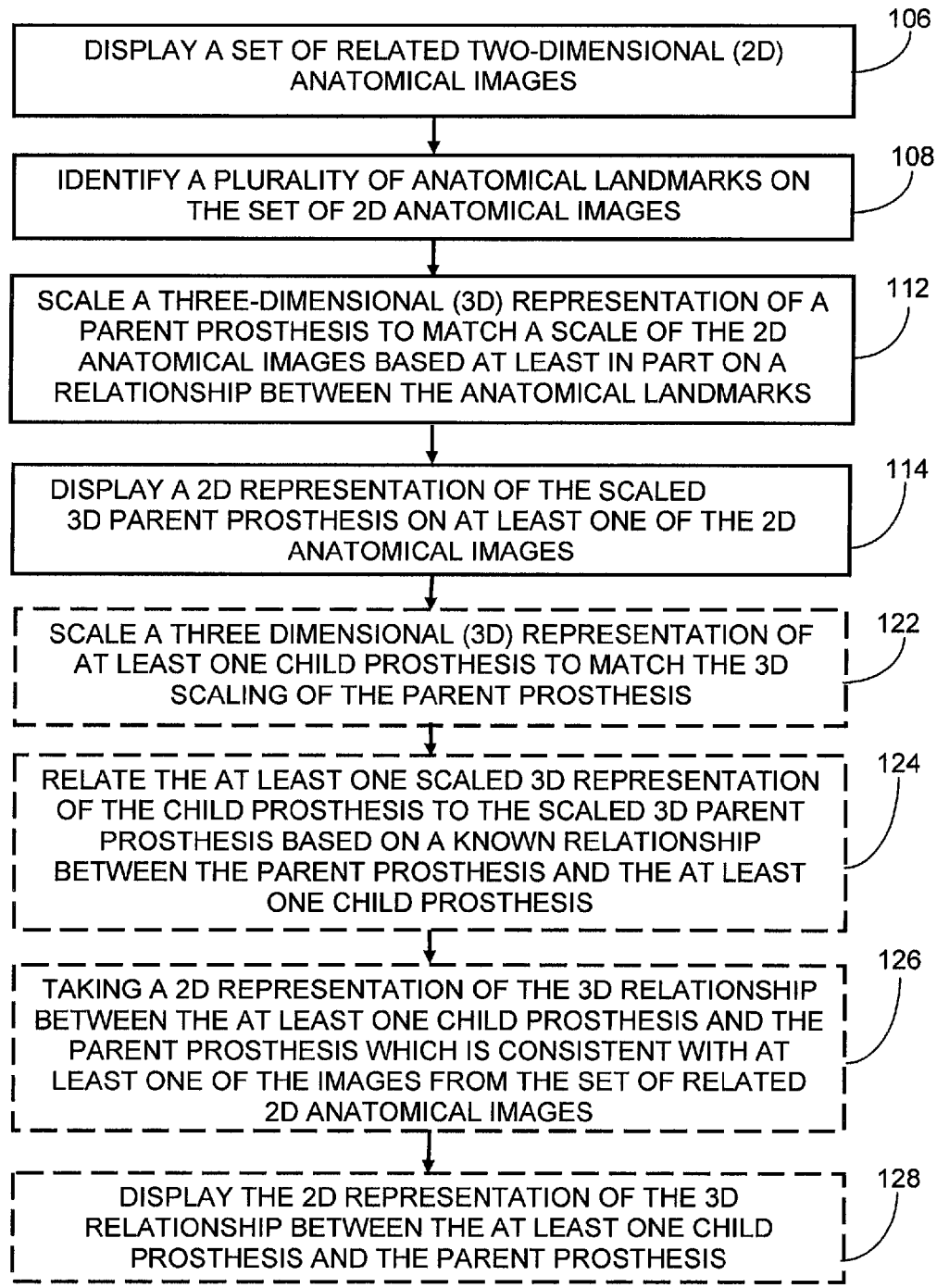
FIG. 10 illustrates another embodiment of a method for surgical planning.

FIG. 10 illustrates another embodiment of a method for surgical planning. Steps 106, 108, 112, and 114 are identical to those discussed above. A set of related 2D anatomical images are displayed. A plurality of anatomical landmarks are identified 108 on the set of 2D anatomical images. A 3D representation of a parent prosthesis is scaled 112 to match a scale of the 2D anatomical images based at least in part on a relationship between the anatomical landmarks. A 2D representation of the scaled 3D parent prosthesis is displayed 114 on at least one of the 2D anatomical images. Optionally, a 3D representation of at least one child prosthesis is scaled 122 to match the 3D scaling of the parent prosthesis. The at least one scaled 3D representation of the child prosthesis may be related 124 to the scaled 3D patient prosthesis based on a known relationship between the parent prosthesis and the at least one child prosthesis. Based on this relationship, the position of the child prostheses may be determined in 3D, and a 2D representation of the 3D relationship between the at least one child prosthesis and the parent prosthesis may be taken 126 which is consistent with at least one of the images from the set of related 2D anatomical images. Finally, the 2D representation of the 3D relationship between the at least one child prosthesis and the parent prosthesis may be displayed 128.

Figure 11:
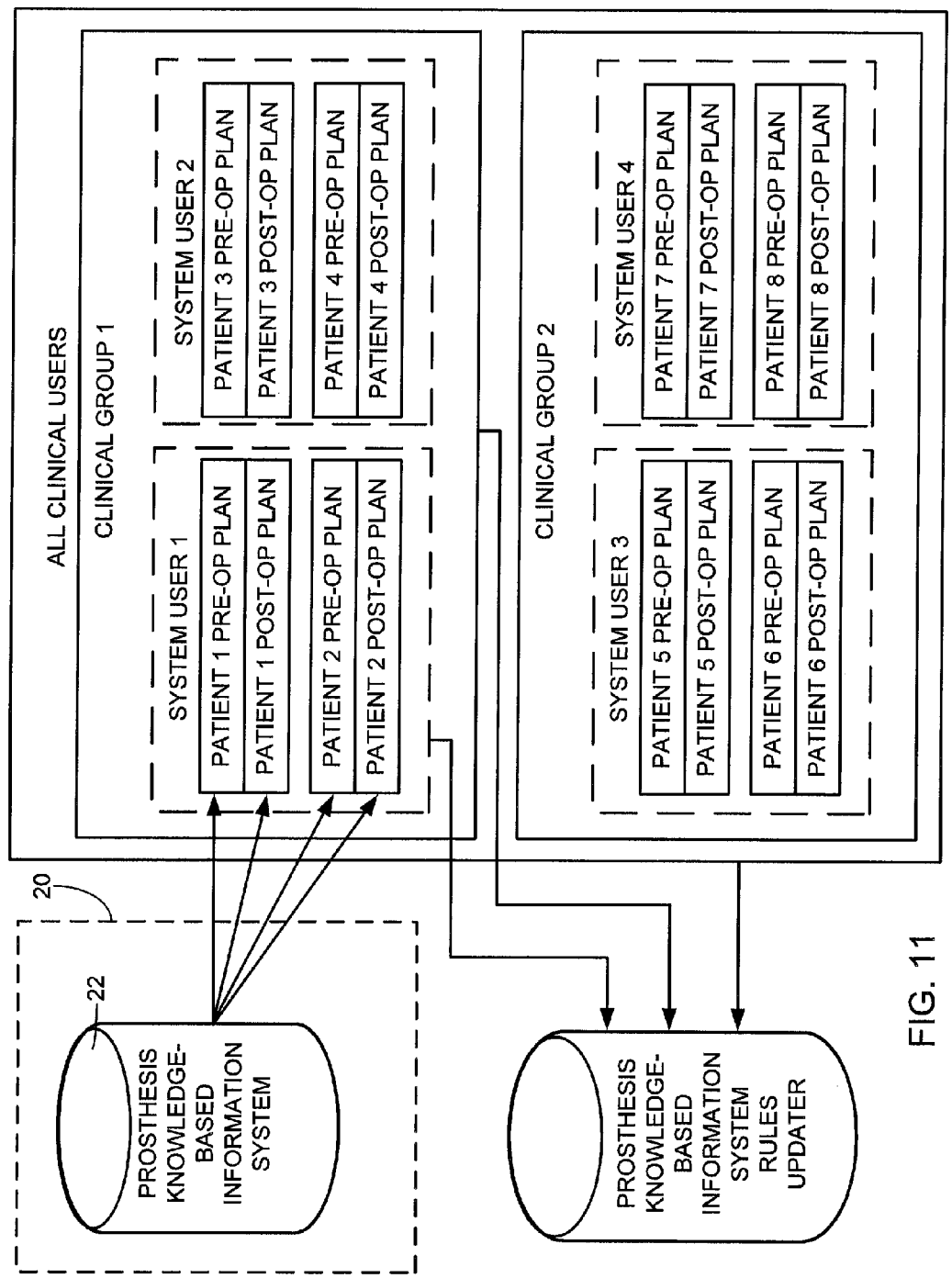
FIG. 11 illustrates one embodiment of how the surgical planning system data can update the prosthesis knowledge based information system.

FIG. 11. illustrates another aspect of the system described and involves the improvement of the prosthesis knowledge based system described as 22 previously in FIG. 1. The prosthesis knowledge based system 22 will have the ability to be modified based on the saved plans and the clinical knowledge contained within. Once the plan is completed for a specific patient by a single clinical user, aspects of the plan including the relative anatomic marker locations and implants selected and it's location will be stored to add rules to the prosthesis knowledge based system for this specific clinician. The pre-operative plan and post-operative review data for the planned case will be included if available based on the clinician's feedback. The more cases planned by the system user, the more the prosthesis knowledge based system 22, will use the new data as a guide to implant selection, placement and contra-indications for the available implants. In addition, some of the clinical data will be available to other system users at the same system sites that will not violate patient or hospital confidentiality. Similarly, an even more limited set of data will be available globally to all system users to tailor the prosthesis knowledge based systems of all users of the system described. This way the prosthesis knowledge based system rules can be updated based upon the real world cases from the system users.

The advantages of a system and method for surgical planning have been discussed herein. Embodiments discussed have been described by way of example in this specification. It will be apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A method for surgical planning, comprising:
displaying a set of related two-dimensional (2D) anatomical images;
identifying a plurality of anatomical landmarks on the set of 2D anatomical images;
creating a 3D anatomical model from the set of related 2D anatomical images using at least one of the plurality of anatomical landmarks, wherein the 3D anatomical model comprises the plurality of anatomical landmarks located in three dimensions;
scaling a three-dimensional (3D) representation of a parent prosthesis to match a scale of the set of related 2D anatomical images based at least in part on a relationship between the plurality of anatomical landmarks;
relating the plurality of anatomical landmarks located in three dimensions to the 3D parent prosthesis; and
displaying a 2D representation of the scaled 3D parent prosthesis on at least one of the set of related 2D anatomical images.

2. The method of claim 1, wherein the set of related 2D anatomical images comprises a set of x-rays, axial CT images that comprise a volume, or 2D images derived from a CT scan, wherein the set of x-rays comprises at least two views.

3. The method of claim 2, wherein the set of x-rays comprises an anterior-posterior (AP) view and a medial lateral view.

4. The method of claim 1, wherein identifying the plurality of anatomical landmarks on the set of related 2D anatomical images comprises selecting at least one anatomical landmark from the group consisting of a pelvis socket, a tear drop line, a greater trochanter, a lesser trochanter, a femoral head, an anatomical mechanical axis.

5. The method of claim 1, wherein identifying the plurality of anatomical landmarks on the set of related 2D anatomical images is performed manually, automatically, or semi-automatically.

6. The method of claim 1, further comprising:
displaying the relationship between the plurality of anatomical landmarks located in three dimensions to the 3D parent prosthesis.

7. The method of claim 1, further comprising:
taking an alternate 2D representation of the 3D relationship between the plurality of anatomical landmarks located in three dimensions and the 3D parent prosthesis.

8. The method of claim 7, further comprising:
displaying the alternate 2D representation of the 3D relationship between the plurality of anatomical landmarks located in three dimensions and the 3D parent prosthesis.

9. The method of claim 1, further comprising:
scaling a three dimensional (3D) representation of at least one child prosthesis to match the 3D scaling of the parent prosthesis;
relating the at least one scaled 3D representation of the child prosthesis to the scaled 3D parent prosthesis based on a known relationship between the parent prosthesis and the at least one child prosthesis; and
taking a 2D representation of the 3D relationship between the at least one child prosthesis and the parent prosthesis which is consistent with at least one of the anatomical images from the set of related 2D anatomical images.

10. The method of claim 9, further comprising:
displaying the 2D representation of the 3D relationship between the at least one child prosthesis and the parent prosthesis.

11. The method of claim 9, further comprising:
updating a process of prosthesis selection based on anatomical landmarks from previously planned cases.

12. A system for surgical planning, comprising:
a prosthesis knowledge-based information system;
a patient anatomical-based information system;
a user interface; and
a controller comprising:
  a) an anatomical landmark identifier;
  b) a prosthesis to anatomical feature relator; and
  c) a three dimensional (3D) model generator,
wherein the controller is configured for displaying a set of related two-dimensional (2D) anatomical images from the patient anatomical-based information system on the user interface,
wherein the anatomical landmark identifier is configured to identify a plurality of anatomical landmarks on the set of related 2D anatomical images using the anatomical landmark identifier,
wherein the 3D model generator is configured to utilize at least two anatomical images from the set of related 2D anatomical images to create a 3D anatomical model,
wherein the 3D anatomical model comprises the plurality of anatomical landmarks located in three dimensions, wherein the prosthesis to anatomical feature relator is configured to scale a three-dimensional (3D) model of a prosthesis from the prosthesis knowledge-based information system to match a scale of the set of related 2D anatomical images based at least in part on a relationship between the plurality of anatomical landmarks, wherein the prosthesis to anatomical feature relator is configured to determine a 3D relationship between the plurality of anatomical landmarks located in three dimensions in the 3D anatomical model and the 3D prosthesis model, and wherein the controller is configured to display a 2D representation of the scaled 3D prosthesis model on at least one of the set of related 2D anatomical images on the user interface.

13. The system of claim 12, wherein the prosthesis knowledge-based information system comprises a database having at least one data field selected from the group consisting of a 3D model of a prosthesis, rotation points of the prosthesis, mechanical axis of a prosthesis, movement of the prosthesis, orientation of the prosthesis, translation of the prosthesis, rotation of the prosthesis, support measurements of the prosthesis, material information for the prosthesis, positional information for the prosthesis, and degrees of freedom for the prosthesis.

14. The system of claim 12, wherein the patient anatomical-based information system comprises a database having at least one data field selected from the group consisting of an x-ray, a CT scan, a patient image, an anatomical landmark, and an anatomical mechanical axis.

15. The system of claim 12, wherein the anatomical landmark identifier is configured to enable a user to identify one or more of the plurality of anatomical landmarks manually via the user interface, wherein the user interface comprises the set of related 2D anatomical images where the plurality of anatomical landmarks are identified, or
wherein the anatomical landmark identifier is configured to identify one or more of the plurality of the anatomical landmarks automatically.

16. The system of claim 12, wherein the controller is further configured for displaying the relationship between the plurality of anatomical landmarks located in three dimensions to the 3D prosthesis model on the user interface.

17. The system of claim 12, wherein the controller further comprises a prosthesis parent to prosthesis child relator configured to determine a 3D relationship between the 3D prosthesis model and a child prosthesis model from the prosthesis knowledge-based information system and the 3D anatomical model.

18. The system of claim 12, wherein the prosthesis knowledge-based information system is updated by plans developed using the system by a clinical user, plans developed using the system by a group of clinical users, or plans developed using the system by all users of the system.

19. A set of machine executable instructions embodied on a machine readable medium for surgical planning, comprising:
instructions displaying a set of related two-dimensional (2D) anatomical images;
instructions identifying a plurality of anatomical landmarks on the set of 2D anatomical images;
instructions creating a 3D anatomical model from the set of related 2D anatomical images using at least one of the plurality of anatomical landmarks, wherein the 3D anatomical model comprises the plurality of anatomical landmarks located in three dimensions;
instructions scaling a three-dimensional (3D) representation of a parent prosthesis to match a scale of the set of related 2D anatomical images based at least in part on a relationship between the plurality of anatomical landmarks;
instructions relating the plurality of anatomical landmarks located in three dimensions to the 3D parent prosthesis; and
instructions displaying a 2D representation of the scaled 3D parent prosthesis on at least one of the set of related 2D anatomical images.

20. The set of machine executable instructions of claim 19, further comprising:
instructions scaling a three dimensional (3D) representation of at least one child prosthesis to match the 3D scaling of the parent prosthesis;
instructions relating the at least one scaled 3D representation of the child prosthesis to the scaled 3D parent prosthesis based on a known relationship between the parent prosthesis and the at least one child prosthesis; and
instructions taking a 2D representation of the 3D relationship between the at least one child prosthesis and the parent prosthesis which is consistent with at least one of the anatomical images from the set of related 2D anatomical images.

21. The set of machine executable instructions of claim 20, further comprising:
displaying the 2D representation of the 3D relationship between the at least one child prosthesis and the parent prosthesis.

\* \* \* \* \*